United States Patent [19]

Holly et al.

[11] 4,130,554
[45] Dec. 19, 1978

[54] PROCESS FOR PREPARING SOMATOSTATIN ANALOG

[75] Inventors: Frederick W. Holly, Glenside; William J. Paleveda, Lansdale; Robert G. Strachan, Warrington; Daniel F. Veber, Ambler, all of Pa.

[73] Assignee: Merck & Co., Inc., Rahway, N.J.

[21] Appl. No.: 566,150

[22] Filed: Apr. 8, 1975

[51] Int. Cl.² .................... C07C 103/52; A61K 37/00
[52] U.S. Cl. ...................... 260/112.5 R; 260/112.5 S; 424/177
[58] Field of Search ................. 260/112.5 R, 112.5 S; 424/177

[56] References Cited

U.S. PATENT DOCUMENTS

| 3,842,066 | 10/1974 | McKinley et al. | 260/112.5 R |
| 3,842,067 | 10/1974 | Sarantakis | 260/112.5 R |
| 3,882,098 | 5/1975 | Sarantakis | 260/112.5 R |
| 3,904,594 | 9/1975 | Guillemin et al. | 260/112.5 S |

OTHER PUBLICATIONS

Berde et al., "Neurohypophysical Hormones and Similar Polypeptides," Handbook of Experimental Pharmacology, vol. 23, Springer-Verlag, Berlin, 1968, pp. 842–845, 856–857, 862.

*Primary Examiner*—Delbert R. Phillips
*Attorney, Agent, or Firm*—Walter Patton; Harry E. Westlake, Jr.

[57] ABSTRACT

Somatostatin analog, hereinafter designated des(Ala¹-Gly²)desaminocys³-somatostatin, having the structure:

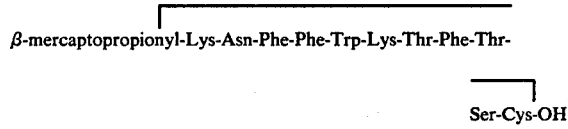

is prepared by controlled stepwise procedures starting with individual amino acid components. This peptide has the property of lowering blood glucose, inhibiting gastric secretion and inhibiting growth hormone release in humans and animals.

9 Claims, No Drawings

PROCESS FOR PREPARING SOMATOSTATIN ANALOG

BACKGROUND OF THE INVENTION

This invention is concerned with the novel long-acting somatostatin analog,

```
┌─────────────────────────────────────────────────┐
β-mercaptopropionyl-Lys-Asn-Phe-Phe-Trp-Lys-Thr-Phe-Thr- ┐
Ser-Cys-OH
``` and the novel process for preparing said somatostatin analog. This invention encompasses the novel blocked β-mercaptopropionyl-containing peptide intermediates, S-Acm-β-mercaptopropionyl-(ε-INOC)Lys-Asn-Phe-Phe-Trp-(ε-INOC)Lys-Thr-Phe-Thr-Ser-(Acm)Cys-OH and S-Acm-β-mercaptopropionyl-Lys-Asn-Phe-Phe-Trp-Lys-Thr-Phe-Thr-Ser-(Acm)Cys-OH useful in the preparation of said analog. All the abbreviations used herein are defined below.

Somatostatin is a tetradecapeptide having the structure:

```
┌─────────────────────────────────────────────┐
Ala-Gly-Cys-Lys-Asn-Phe-Phe-Trp-Lys-Thr-Phe-Thr-Ser-Cys-OH
``` and is known to inhibit the release of growth hormone. Somatostatin itself has a short duration of action because it is inactivated, inter alia, by aminopeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to hydrolysis by aminopeptidases than somatostatin itself. The present invention provides a somatostatin analog having the biological activity of somatostatin and a longer duration of action and a novel method for preparing said analog. The somatostatin analog of the present invention differs from somatostatin itself by virtue of the fact that the component Ala-Gly-Cys-OH in somatostatin is replaced by the β-mercaptopropionyl group. This somatostatin analog, designated des(Ala$^1$-Gly$^2$)desaminocys$^3$-somatostatin, has no α-amino group, thus eliminating one of the groups involved in enzymatic cleavage of the molecule. Therefore, this analog is resistant to cleavage in vivo by aminopeptidases and thus has a prolonged duration of action.

The abbreviated designations, which are used herein for the amino acid components, certain preferred protecting groups, amino acid activation groups, condensing agents, reagents and solvents employed in the process of this invention are as follows:

| Abbreviated Designation | Amino Acid |
|---|---|
| Lys | L-lysine |
| Asn | L-asparagine |
| Phe | L-phenylalanine |
| Trp | L-tryptophan |
| Thr | L-threonine |
| Ser | L-serine |
| Cys | L-cysteine |

| Abbreviated Designation | Protecting Groups |
|---|---|
| Acm | acetamidomethyl |
| INOC | isonicotinyloxycarbonyl |
| BOC | tert-butyloxycarbonyl |
| OMe | methyl ester |

| Abbreviated Designation | Activating Groups |
|---|---|
| NPE | p-nitrophenyl ester |
| HSE | N-hydroxysuccinimide ester |
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |
| DNTB | 5,5'-dithiobis-(2-nitrobenzoic acid) |

| Abbreviated Designation | Solvents |
|---|---|
| EPAW | ethyl acetate-pyridine-acetate acid-water |
| BAW | butanol-acetic acid-water |
| CMW | chloroform-methanol-water |
| DMF | dimethylformamide |
| THF | tetrahydrofuran |

SUMMARY OF THE INVENTION

In accordance with the process of the present invention, des(Ala$^1$-Gly$^2$)desaminocys$^3$-somatostatin is prepared by stepwise coupling, by peptide linkages, of each of its individual amino acid components, which peptide coupling is conducted by reacting the appropriate amino acid in the sequence (as a derivative in which the carboxyl group is activated and any amino and sulfhydryl groups are protected) first with Acm-Cys (the amino acid at the C-terminus, i.e. the carboxy end of the reduced form of des(Ala$^1$-Gly$^2$)desaminocys$^3$-somatostatin), and then subsequently with each resulting peptide intermediate, such a stepwise method being referred to herein as sequential synthesis. It is ordinarily preferred to utilize, as the carboxyl activated amino acid an activated ester such as the HSE, NPE or HBT ester of such amino acid; or the amino acid azide.

The term "reduced" or "linear" form of des(Ala$^1$-Gly$^2$)desaminocys$^3$-somatostatin refers to a linear undecapeptide having the structure: β-mercaptopropionyl-Lys-Asn-Phe-Phe-Trp-Lys-Thr-Phe-Thr-Ser-Cys-OH. This peptide is also designated des(Ala$^1$-Gly$^2$)-desaminocys$^3$-dihydrosomatostatin.

Instead of sequential synthesis, des(Ala$^1$-Gly$^2$)-desaminocys$^3$-somatostatin can also be prepared, according to the process of this invention, by block synthesis, wherein various peptide segments of des(Ala$^1$-Gly$^2$)desaminocys$^3$-somatostatin are individually synthesized, and these segments are then coupled in proper sequence to form the desired product. These peptide segments are themselves conveniently prepared by sequential synthesis in solution using the HSE, NPE or HBT active ester procedure or the azide procedure. The number of amino acid components in the peptide segments used in block synthesis of des(Ala$^1$-Gly$^2$)-desaminocys$^3$-somatostatin may vary from two to nine, but peptide segments containing seven amino acid components or less are preferably utilized, thus avoiding condensations involving larger peptide segments with attendant losses of these more valuable higher peptide fragments.

In carrying out these sequential or block syntheses, involving reaction between carboxyl (or activated carboxyl) of one amino acid and amino group of the other, it is ordinarily preferred to protect the amino and sulfhydryl groups in the amino acid or peptide undergoing reaction at the carboxyl end of the molecule, as well as other functional groupings in both reactants reactive under the conditions of such synthesis. Protecting groups must retain their protecting properties under the peptide coupling conditions, and must be selectively removable without affecting peptide linkages. Protecting groups to be removed following a particular step must also be selectively removable without affecting other protecting groups to be retained in later coupling steps.

Amino-protecting groups ordinarily employed include acyl-type substituents such as formyl, phthalyl, trifluoroacetyl, toluenesulfonyl, dibenzylphosphoryl, nitrophenylsulfenyl, tritylsulfenyl, o-nitrophenoxyacetyl, and the like, urethane-type protecting substituents such as benzyloxycarbonyl (carbobenzoxy), p-methoxycarbobenzoxy, p-nitrocarbobenzoxy, t-butyloxycarbonyl, 2-(p-biphenylyl)-2-isopropyloxycarbonyl, isonicotinyloxycarbonyl, and the like, alkyl-type substituents such as triphenylmethyl, trialkylsilyl, trimethylsilyl, and the like. The group preferred for protecting the ε-amino group of lysine is isonicotinyloxycarbonyl. It is preferred to utilize tert-butyl-oxycarbonyl (BOC) for protecting the α-amino group in the amino acids (or peptides) undergoing reaction at the carboxyl end of the molecule, since the BOC protecting group is readily removed following such reaction and prior to the subsequent step (wherein such α-amino group itself undergoes reaction) by relatively mild action of acids (e.g. trifluoroacetic acid, or hydrogen chloride in ethyl acetate) which treatment does not affect groupings, such as carbobenzoxy (Cbz) and isonicotinyloxycarbonyl, used to protect other amino groups such as the basic amino group of lysine. The carbobenzoxy group is removable by treatment with hydrogen bromide in glacial acetic acid or hydrogen fluoride, which treatment does not affect the isonicotinyloxycarbonyl group. The removal with hydrogen fluoride is facilitated by the presence of anisole. The isonicotinyloxycarbonyl group is removable by the action of zinc.

Sulfhydryl-protecting groups ordinarily employed include benzyl, p-nitrobenzyl, trityl, diphenylmethyl, benzylthiomethyl, carbobenzoxy and acetamidomethyl. The preferred group for protecting the sulfhydryl group of cysteine is the acetamidomethyl group hereinafter referred to as Acm.

Carboxyl-protecting groups ordinarily employed include amides, salt formation, ester substituents such as the methyl and ethyl esters (which are preferred where subsequent conversion, via the hydrazide, to the azide is desired), the benzyl ester, p-nitrobenzylester, t-butyl ester, and the like. Hydroxyl groups are ordinarily not protected in the synthesis of des(Ala$^1$-Gly$^2$)-desaminocys$^3$-somatostatin where the coupling reactions are conducted in solution, although tetrahydropyranyl, benzyltrifluoroacetyl, t-butyl, and the like, may be used for such protection if desired.

The selection of protecting groups is in part dictated by particular coupling conditions, in part by the amino acid and peptide components involved in the reaction.

Guides for selecting particular protecting groups to be employed herein are set forth in detail in the French Pat. No. 1,496,536, and the protecting groups disclosed in that patent are incorporated herein by reference.

DESCRIPTION OF THE PREFERRED EMBODIMENTS

The preferred overall procedure for the preparation of des(Ala$^1$-Gly$^2$)desaminocys$^3$-somatostatin is outlined diagrammatically in Table 1 as follows:

TABLE 1

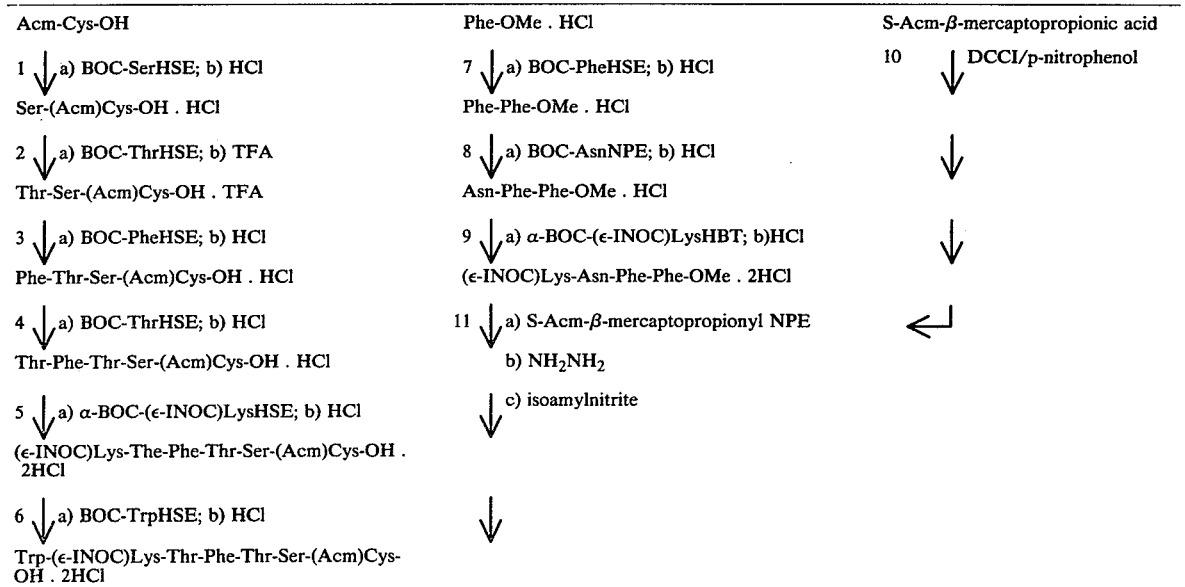

TABLE 1-continued

12 ↓ a) S-Acm-β-mercaptopropionyl-(ε-INOC)Lys-Asn-Phe-Phe-N₃
  ↓ b) Zn

S-Acm-β-mercaptopropionyl-Lys-Asn-Phe-Phe-Trp-Lys-Thr-Phe-Thr-Ser-(Acm)Cys-OH

13 ↓ a) Hg(OAc)₂, mercaptoethanol, Sephadex G-10 gel filtration
  ↓ b) Cu, O₂  ┌─────────────────────────────────────────────┐
β-mercaptopropionyl-Lys-Asn-Phe-Phe-Trp-Lys-Thr-Phe-Thr-Ser-Cys-OH In Table 1 the number appearing to the left of each arrow refers to the illustrative Example which sets forth the experimental details for the indicated conversion.

This preferred overall procedure involves combinations of sequential and block synthesis, wherein certain peptide segments of des(Ala¹-Gly²)-desaminocys³-somatostatin are initially formed by the stepwise method, by sequential synthesis in solution, and these segments are then coupled in proper sequence. In this procedure, the BOC substituent is used to protect α-amino groups, the acetamidomethyl group, Acm, is used to protect the sulfhydryl group of cysteine and the sulfhydryl group of β-mercaptopropionic acid; the isonicotinyloxycarbonyl group, INOC, is used to protect the ε-amino group of lysine and the methyl ester group is used to protect the carboxyl group of phenylalanine, phenylalanyl-phenylalanine, asparaginyl-phenylalanyl-phenylalanine, (ε-INOC)lysyl-asparaginyl-phenylalanyl-phenylalanine and S-Acm-β-mercaptopropionyl-(ε-INOC)lysyl-asparaginyl-phenylalanyl-phenylalanine. In the case of S-Acm-β-mercaptopropionyl-(ε-INOC)lysyl-asparaginyl-phenylalanyl-phenylalanine, the methyl ester serves the further purpose of providing the intermediate for preparing, via the hydrazide, S-Acm-β-mercaptopropionyl-(ε-INOC)lysyl-asparaginyl-phenylalanyl-phenylalanine azide. Instead of this preferred method, however, the present invention also contemplates the various permutations of alternate routes, and employment of other protecting groupings fulfilling criteria hereinabove discussed, such alternate routes likewise involving sequential synthesis in solution, and combinations of sequential and block synthesis procedures.

As reference to Table 1 will show, one preferred overall procedure for preparing des(Ala¹-Gly²)-desaminocys³-somatostatin specifically involves (a) sequential synthesis of the C-terminal heptapeptide segment, Trp-(ε-INOC)Lys-Thr-Phe-Thr-Ser-(Acm)Cys-OH, and (b) the N-terminal tetrapeptide segment, S-Acm-β-mercaptopropionyl-(ε-INOC)Lys-Asn-Phe-Phe-azide, (c) condensing the peptides prepared in steps (a) and (b) to form the peptide S-Acm-β-mercaptopropionyl-(ε-INOC)Lys-Asn-Phe-Phe-Trp-(ε-INOC)Lys-Thr-Phe-Thr-Ser-(Acm)Cys-OH, (d) removing the protective groups, INOC and Acm and, (e) cyclyzing the resulting unblocked undecapeptide to obtain the novel somatostatin analog des(Ala¹-Gly²)desaminocys³-somatostatin.

The C-terminal heptapeptide segment is prepared by reacting Acm-Cys-OH.HCl with BOC-SerHSE. The Acm-Cys-OH hydrochloride is converted to the free amine with a weak base and reacted with BOC-SerHSE dissolved in a suitable organic solvent such as ethanol. The reaction is conducted by bringing the solutions together and stirring at room temperature at approximately neutral pH but preferrably at a pH of 6.8 to 8, under which conditions the reaction is ordinarily complete in about 2 hours. The solution is acidified and the organic solvent evaporated. The remaining aqueous solution is lyophilized. The lyophilized solid is purified by chromatography to give substantially pure BOC-Ser-(Acm)Cys-OH. This dipeptide is treated with anhydrous hydrogen chloride gas in ethyl acetate, thereby cleaving the BOC substituent to form Ser-(Acm)Cys-OH hydrochloride.

This Ser-(Acm)Cys-OH hydrochloride is converted to the free amine with a weak base in water and reacted with a solution of BOC-ThrHSE in a suitable organic solvent, such as ethanol, which reaction is conducted by bringing the solutions together and stirring at room temperature for about 4 hours. The solution is evaporated to dryness. The residue is dissolved in a suitable organic solvent and the insoluble salt removed by filtration. The crude product is purified by chromatography to give substantially pure BOC-Thr-Ser-(Acm)Cys. This tripeptide is treated with TFA, thereby cleaving the BOC substituent to form Thr-Ser-(Acm)Cys-OH.TFA.

The tripeptide, Thr-Ser-(Acm)Cys-OH.TFA, is converted to the free amine with a weak base in water and reacted with a slurry of BOC-PheHSE in a suitable organic solvent, which reaction is conducted by vigorously agitating the reactants together overnight at room temperature. The reaction solution is evaporated to dryness, dissolved in a minimum amount of water and acidified to give a substantially pure precipitate of BOC-Phe-Thr-Ser-(Acm)Cys-OH. This tetrapeptide is treated with anhydrous hydrogen chloride in ethyl acetate, thereby cleaving the BOC group to give the substantially pure tetrapeptide Phe-Thr-Ser-(Acm)Cys-OH hydrochloride.

The tetrapeptide, Phe-Thr-Ser-(Acm)Cys-OH hydrochloride is converted to the free base with a weak base in water and reacted with BOC-ThrHSE in a suitable organic solvent, such as ethanol, which reaction is conducted by vigorously agitating the reactants together overnight at room temperature. The solution is acidified and the precipitate of crude product is collected and recrystallized to give substantially pure pentapeptide, BOC-Thr-Phe-Thr-Ser-(Acm)Cys-OH. This pentapeptide is treated with anhydrous hydrogen chloride in ethyl acetate, thereby cleaving the BOC substituent to form Thr-Phe-Thr-Ser-(Acm)Cys-OH hydrochloride.

α-BOC-(ε-INOC)Lys-OH is reacted with N-hydroxysuccinimide in the presence of DCCI. The resulting α-BOC-(ε-INOC)LysHSE is reacted with the pentapeptide Thr-Phe-Thr-Ser-(Acm)Cys-OH hydrochloride which reaction is conducted by contacting the reactants together in freshly degassed DMF at a pH of about neutral, preferably at a pH of about 7.7 to about 8.0 overnight. The solution is evaporated to an oil. The oil is dissolved in a minimum amount of EPAW (10:5:1:3), the insolubles filtered out and the filtrate containing the crude product is purified by chromatography to give substantially pure blocked hexapeptide α-BOC-(ε-INOC)Lys-Thr-Phe-Thr-Ser-(Acm)Cys- OH. The blocked hexapeptide is treated with anhydrous hydrogen chloride in ethyl acetate, thereby cleaving the BOC substituent to form the hexapeptide (ε-INOC)Lys-Thr-Phe-Thr-Ser-(Acm)Cys-OH dihydrochloride.

The hexapeptide (ε-INOC)Lys-Thr-Phe-Thr-Ser-(Acm)Cys-OH dihydrochloride is converted to the free base with a weak base in water and reacted with a solution of BOC-TrpHSE in a suitable organic solvent, such as DMF, at about a neutral pH, preferably at about 7.5 to about 7.1, under which conditions the reaction is complete in about 2 to 3 hours. The reaction solution is acidified and concentrated to dryness to yield a crude oil. This oil is dissolved in EPAW (10:5:1:3) and chromatographed to give substantially pure blocked heptapeptide BOC-Trp-(ε-INOC)Lys-Thr-Phe-Thr-Ser-(Acm)Cys-OH. The blocked heptapeptide is treated with anhydrous hydrogen chloride in ethyl acetate, thereby cleaving the BOC substituent to form the C-terminal heptapeptide Trp-(ε-INOC)Lys-Thr-Phe-Thr-Ser-(Acm)Cys-OH dihydrochloride.

The N-terminal tetrapeptide S-Acm-β-mercaptopropionyl-(ε-INOC)Lys-Asn-Phe-Phe azide is prepared by reacting Phe-OME hydrochloride with BOC-PheHSE, which reaction is conducted in a suitable organic solvent, such as chloroform or methylene chloride, overnight at a basic pH. Insoluble materials are separated and the organic solution evaporated to dryness and the residue recrystallized. The blocked dipeptide is treated with anhydrous hydrogen chloride in ethyl acetate, thereby cleaving the BOC substituent to form Phe-Phe-OMe hydrochloride.

The dipeptide Phe-Phe-OMe hydrochloride is reacted with BOC-AsnNPE in a suitable organic solvent such as DMF at neutral pH preferably at about a pH of 7.2 overnight. The reaction solution is concentrated and the residue dissolved in chloroform. The organic solution is washed and evaporated to dryness. The residue is recrystallized to give substantially pure BOC-Asn-Phe-Phe-OMe. The blocked tripeptide is treated with anhydrous hydrogen chloride in ethyl acetate, thereby cleaving the BOC substituent to form Asn-Phe-Phe-OMe hydrochloride.

α-BOC-(ε-INOC)Lys is reacted with 1-hydroxybenzotriazole, HBT, in the presence of DCCI in a suitable organic solvent such as DMF to form α-BOC-(ε-INOC)LysHBT. To this solution is added Asn-Phe-Phe-OMe hydrochloride. The pH of the reaction is adjusted to about neutral and stirred overnight. The reaction mixture is filtered to remove dicyclohexylurea and evaporated to dryness. The residue is suspended in a suitable organic solvent and collected by filtration. The blocked tetrapeptide is treated with anhydrous hydrogen chloride in ethyl acetate, thereby cleaving the BOC substituent to form (ε-INOC)Lys-Asn-Phe-Phe-OMe dihydrochloride.

S-Acm-β-mercaptopropionylNPE is formed by treating a solution of S-Acm-β-mercaptopropionic acid with p-nitrophenol in the presence of DCCI. After removing solids by filtration, the filtrate is concentrated to a small volume and the desired S-Acm-β-mercaptopropionylNPE crystallizes.

A solution of (ε-INOC)Lys-Asn-Phe-Phe-OMe dihydrochloride is treated with S-Acm-β-mercaptopropionylNPE at a basic pH preferably at about pH 8 overnight. The reaction solution is evaporated and the residue purified by chromatography to give substantially pure tetrapeptide, S-Acm-β-mercaptopropionyl-(ε-INOC)Lys-Asn-Phe-Phe-OMe.

This tetrapeptide is dissolved in a solution of methanol-hydrazine to convert the methyl ester group to the hydrazide. The resulting hydrazide, slurried in a suitable organic solvent such as DMF, is treated with isoamyl nitrite at −25° C. thereby yielding a cold solution containing S-Acm-β-mercaptopropionyl-(ε-INOC)Lys-Asn-Phe-Phe-N₃ which is immediately reacted with a cold solution of Trp-(ε-INOC)Lys-Thr-Phe-Thr-Ser-(Acm)Cys-OH dihydrochloride to give the novel blocked undecapeptide S-Acm-β-mercaptopropionyl-(ε-INOC)Lys-Asn-Phe-Phe-Trp-(ε-INOC)Lys-Thr-Phe-Thr-Ser-(Acm)Cys-OH.

This blocked undecapeptide is treated with freshly-activated zinc dust in 50% aqueous acetic acid, thereby cleaving the ε-INOC substituents from the lysine amino acids. The mixture is filtered to remove unreacted Zn and the crude product in the filtrate is purified by chromatography to yield the novel undecapeptide, 5-Acm-β-mercaptopropionyl-Lys-Asn-Phe-Phe-Tro-Lys-Thr-Phe-Thr-Ser-(Acm)Cys in substantially pure form.

The undecapeptide is treated with a mercuric ion containing salt such as mercuric acetate, mercuric chloride and the like in dilute acetic acid thereby removing the Acm group from the β-mercaptopropionyl component of the peptide and from the cysteine amino acid. The reaction is completed after stirring overnight after which mercaptoethanol is added and the product purified by chromatography to give the fully unblocked undecapeptide, β-mercaptopropionyl-Lys-Asn-Phe-Phe-Trp-Lys-Thr-Phe-Thr-Ser-Cys-OH.

A solution of this unblocked undecapeptide in dilute acetic acid is adjusted to about pH 8 and stirred overnight at room temperature in the presence of atmospheric oxygen and a trace amount of copper ion wherein the copper ion is provided by the presence in the reaction vessel of elemental copper. After removing the copper, the reaction solution is evaporated to dryness or lyophilized and the residue purified by chromatography to give substantially pure novel somatostatin analog, des(Ala¹-Gly²)desaminocys³-somatostatin.

Alternatively, the undecapeptide, S-Acm-β-mercaptopropionyl-Lys-Asn-Phe-Phe-Trp-Lys-Thr-Phe-Thr-Ser-(Acm)Cys-OH, may be treated with iodine in glacial acetic acid, from 1 to 7 days, thereby removing the Acm groups from the β-mercaptopropionyl component of the peptide and from the cysteine amino acid and simultaneously oxidizing the free sulfhydryl groups to obtain the novel somatostatin analog des(Ala¹-Gly²)-desaminocys³-somatostatin.

The following Examples illustrate methods of carrying out the present invention, but it is to be understood that these Examples are given for purposes of illustration and not of limitation.

EXAMPLE 1

Preparation of Ser-(Acm)Cys-OH Hydrochloride

Step a

To a solution of 10.97 g. of Acm-Cys-OH in 110 ml. water is added 12.07 g. sodium bicarbonate and a solution of 14.49 g. BOC-SerHSE in 145 ml. of 95% ethanol. The reaction mixture, which has a pH of 6.8, becomes clear after stirring for 2 hours. The pH of the solution is adjusted to 2.5 with concentrated HCl. The acidified solution is evaporated in vacuo to remove the ethanol. The remaining aqueous solution is lyophilized.

The lyophilized solid is dissolved in a minimum amount of EPAW (ethyl acetate:pyridine:acetic acid:water 10:5:1:3) and applied on an 8 cm. × 71.5 cm. column packed with Silica Gel 60 and eluted with EPAW (10:5:1:3). Twenty ml. fractions are collected. The fractions containing the product, as identified by thin layer chromatography, are combined and concentrated in vacuo. The residue is triturated with ethyl acetate, filtered, washed with ethyl acetate and dried in vacuo. The weight of the BOC-Ser-(Acm)Cys-OH, obtained as a dry solid, is 13.91 g.

Step b

BOC-Ser-(Acm)Cys-OH, 6.56 g., is suspended in 100 ml. anhydrous ethyl acetate. The mixture is cooled in an ice bath while a vigorous stream of anhydrous HCl gas is bubbled in for 10 minutes. The mixture is concentrated in vacuo to near dryness, the solid is washed several times with ethyl acetate and dried in vacuo. To insure complete reaction, the solid is again treated with HCl gas for 10 minutes as above in ethyl acetate. The mixture is concentrated in vacuo. The solid residue is filtered, washed with ethyl acetate and dried in vacuo to yield 5.55 g. of Ser-(Acm)Cys-OH hydrochloride.

EXAMPLE 2

Preparation of Thr-Ser-(Acm)Cys-OH.TFA

Step a

To a solution of 5.55 g. Ser-(Acm)Cys-OH.HCl in 55 ml. water is added, with stirring, 4.36 g. sodium bicarbonate. The pH of the resulting solution is 7.05. To this solution is added 5.47 g. BOC-ThrHSE in 55 ml. of 95% ethanol. After the addition is complete, the pH is 7.1. After 4 hours of stirring at room temperature, the pH of the reaction mixture is 7.8. The pH is adjusted to 3.8 by the addition of 11 ml. 2.5N HCl to give a clear solution. The solution is evaporated to dryness in vacuo.

The residue is dissolved in 25 ml. 95% ethanol. The insoluble NaCl is centrifuged off. 15.2 g. of crude BOC-Thr-Ser-(Acm)Cys-OH prepared by the above process is applied on a column containing 3,600 g. dry Silica Gel 60, eluted with EPAW 10:5:1:3 and 20.6 ml. fractions collected. The fractions containing the product, as identified by thin layer chromatography, are combined and evaporated to dryness in vacuo. The residue is washed with ethyl acetate, filtered, washed with ethyl acetate again and dried in vacuo to yield 12.13 g. of BOC-Thr-Ser-(Acm)Cys-OH.

Step b

BOC-Thr-Ser-(Acm)Cys-OH, 12.0 g., is suspended in 35 ml. TFA at 0° C. and allowed to come to room temperature during which time complete solution occurs. The TFA solution is poured into 700 ml. petroleum ether with stirring. The product separates as an oil and the supernatant is decanted. The oily residue is dissolved in 200 ml. ethyl acetate and precipitated with 400 ml. petroleum ether. The supernatant is decanted from the mill somewhat oily residue. Petroleum ether, 500 ml., is added to the residue. After trituration the resulting solid product is filtered, washed with petroleum ether and dried in vacuo to give 13.48 g. of Thr-Ser-(Acm)Cys-OH.TFA.

EXAMPLE 3

Preparation of Phe-Thr-Ser-(Acm)Cys-OH Hydrochloride

Step a

Thr-Ser-(Acm)Cys-OH.TFA, 13.43 g., is dissolved in 122 ml. water with stirring. To this solution is added 6.28 g. of sodium bicarbonate in portions and 9.05 g. BOC-PheHSE slurried in 122 ml. ethanol. The resulting cloudy solution is stirred overnight at room temperature. The reaction solution is concentrated in vacuo to a viscous oil. Enough water is added to dissolve the oil. The solution is acidified with 2.5N HCl to a pH of 2. The resulting solid is filtered, washed with 750 ml. water, dried by suction on a funnel, and washed with 275 ml. of ethyl acetate. The washed solid is dried overnight in vacuo at room temperature to yield 10.63 g. BOC-Phe-Thr-Ser-(Acm)Cys-OH.

Step b

BOC-Phe-Thr-Ser-(Acm)Cys-OH, 1.23 g., is suspended in 20 ml. ethyl acetate. The mixture is cooled in an ice bath while a vigorous stream of anhydrous HCl gas is bubbled in for 10 minutes with stirring. The reaction mixture sets solid. The solid cake is allowed to stand 10 minutes in the ice bath. Nitrogen gas is bubbled in for 10 minutes at ice bath temperature and for 5 minutes at room temperature. Additional ethyl acetate is added and the solid cake is broken up. The solid is filtered under nitrogen, slurried three times with ethyl acetate and dried with a stream of nitrogen to yield 1.18 g. of Phe-Thr-Ser-(Acm)Cys-OH hydrochloride.

EXAMPLE 4

Preparation of Thr-Phe-Thr-Ser-(Acm)Cys-OH Hydrochloride

Step a

Phe-Thr-Ser-(Acm)Cys-OH.HCl, 10.05 g., is dissolved in 110 ml. water. To this solution is added 4.49 g. of sodium bicarbonate in portions. A solution of 6.2 g. (10% excess) BOC-ThrHSE in 55 ml. ethanol is added with stirring. The reaction solution is stirred overnight at room temperature. The solution is acidified to pH 2 with 2.5N HCl. The solid is filtered out and washed with a small volume of ethyl acetate and dried overnight in vacuo to yield 10.53 g. of crude BOC-Thr-Phe-Thr-Ser-(Acm)Cys-OH. The crude solid, 10.5 g., is dissolved in a minimum amount of refluxing methanol:water, 9:1 and kept at room temperature overnight. The crystals are collected by filtration, washed with methanol and dried in vacuo to yield 8.25 g. of pure BOC-Thr-Phe-Thr-Ser-(Acm)Cys-OH.

Step b

BOC-Thr-Phe-Thr-Ser-(Acm)Cys-OH, 8.1 g., is suspended in 100 ml. ethyl acetate. The slurry is cooled to 0° C. in an ice bath and anhydrous HCl gas bubbled in for 15 minutes with stirring. Nitrogen is bubbled in vigorously for 15 minutes. The solid is filtered, washed twice with ethyl acetate and dried in vacuo overnight to yield 7.85 g. of Thr-Phe-Thr-Ser-(Acm)Cys-OH hydrochloride.

EXAMPLE 5

Preparation of (ε-INOC)Lys-Thr-Phe-Thr-Ser-(Acm)Cys-OH Dihydrochloride

Step a

α-BOC-(ε-INOC)Lys-OH, 6.34 g., is dissolved in 166.5 ml. freshly degassed DMF. To this solution is added 1.916 g. N-hydroxysuccinimide and the mixture stirred until complete solution occurs. To this solution is added 2.75 g. DCCI and the reaction solution is stirred overnight at room temperature. To this solution is added 7.75 g. Thr-Phe-Thr-Ser-(Acm)Cys-OH hydrochloride dissolved in 45 ml. DMF. The pH of the solution is adjusted to 7.7 by the addition of 4.9 ml. TEA. After stirring for 15 minutes, the pH becomes 8. The reaction solution is allowed to stand overnight and then concentrated in vacuo to a viscous, reddish-brown oil.

The oil is dissolved in a minimum amount of EPAW (10:5:1:3). The insolubles are removed by filtration and the filtered solution applied on a column packed with 3,600 ml. of dry Silica Gel H. The dry column is developed by gravity flow with EPAW (10:5:1:3) and 20 ml. fractions are collected. The fractions containing the product, as identified by thin layer chromatography, are combined and concentrated in vacuo. The residue is flushed and triturated with ethyl acetate to obtain a filterable solid. The solid is filtered, washed with ethyl acetate and dried in vacuo to give 4.88 g. of the blocked hexapeptide α-BOC-(ε-INOC)Lys-Thr-Phe-Thr-Ser-(Acm)Cys-OH.

Step b

The blocked hexapeptide, 4.6 g., is slurried in 46 ml. ethyl acetate and cooled in an ice bath. A vigorous stream of anhydrous HCl gas is bubbled into the suspension for 15 minutes. The reaction mixture is stirred at 0° C. for 15 minutes more and then purged with a stream of nitrogen for 15 minutes. The solid is filtered, washed with ethyl acetate and dried overnight in vacuo to yield 4.01 g. of (ε-INOC)Lys-Thr-Phe-Thr-Ser-(Acm)Cys-OH dihydrochloride.

EXAMPLE 6

Preparation of Trp-(ε-INOC)Lys-Thr-Phe-Thr-Ser-(Acm)Cys-OH Dihydrochloride

Step a (ε-INOC)-Lys-Thr-Phe-Thr-Ser-(Acm)Cys-OH dihydrochloride, 442.3 mg., is dissolved in 9.5 ml. water. To this solution is added 120.1 mg. sodium bicarbonate. A clear solution of pH 7.5 is obtained. However, after a few minutes, solid begins to precipitate. To this suspension is added a solution of 191.1 mg. BOC-TrpHSE in 4.75 ml. freshly degased DMF. After 1 hour, 4.75 ml. of DMF is added in order to completely dissolve solids precipitating from the reaction solution. After 2 hours and 40 minutes, the pH of the reaction solution is 7.1. Three drops of 2.5N HCl are added to adjust the pH to 5.8 determined by moist indicator paper and the solution concentrated to dryness in vacuo to yield an oily residue. This oily residue is dissolved in 10 ml. EPAW (10:5:1:3) and 2 ml. acetic acid and applied on a 3.3 cm. diameter column packed to a height of 14 cm. with dry Silica Gel H and eluted with EPAW (10:5:1:3) and 6.1 ml. fractions are collected. The fractions containing the product, as identified by thin layer chromatography, are combined and evaporated to dryness in vacuo. The resulting partially-solidified oil is flushed twice with ethyl acetate and triturated with ethyl acetate until the oil solidifies. The solid is filtered, slurried twice with ethyl acetate and dried in vacuo to yield 0.4 g. of the blocked heptapeptide, BOC-Trp-(ε-INOC)Lys-Thr-Phe-Thr-Ser-(Acm)Cys-OH.

Step b

The blocked heptapeptide, 346.9 mg., is suspended in 3.5 ml. ethyl acetate to which suspension is added 0.35 ml. mercaptoethanol. This suspension is cooled in an ice bath. A vigorous stream of anhydrous HCl gas is bubbled in for 10 minutes, after which the reaction mixture is purged with nitrogen gas for 15 minutes. The solid is filtered under nitrogen, slurried four times with ethyl acetate and dried with a stream of nitrogen. The solid is kept under vacuo overnight to remove traces of mercaptoethanol. The dried solid, Trp-(ε-INOC)Lys-Thr-Phe-Thr-Ser-(Acm)Cys-OH dihydrochloride, weighs 380.7 mg.

EXAMPLE 7

Preparation of Phe-Phe-OMe Hydrochloride

Step a

To a suspension of 10.78 g. Phe-OMe hydrochloride in 500 ml. methylene chloride is added 18.0 g. BOC-PheHSE. The pH is adjusted to 9 with triethylamine to give a clear solution. This solution is allowed to stand overnight. Precipitated solids are filtered out and washed with methylene chloride. The methylene chloride filtrate and washings, containing the product, are combined and washed with saturated sodium chloride solution (2 × 500 ml.); 10% sodium bicarbonate solution (2 × 500 ml.) and with 0.1N $H_2SO_4$ (2 × 250 ml.). The washes are back washed with methylene chloride (1 × 200 ml.). The combined methylene chloride solutions are dried over anhydrous sodium sulfate, filtered and evaporated to dryness. The residue is recrystallized from methylene chloride-hexane to obtain 9 g. of the blocked dipeptide BOC-Phe-PheOMe, m.p. 122.0°–122.5° C.

Calculated for BOC-Phe-PheOMe: C, 67.57; H, 7.09; N, 6.57. Found: C, 67.67; H, 7.37; N, 6.31.

A second crop of crystals is obtained from the filtrates, weight 11 g.

Step b

The blocked dipeptide, 3.0 g., is suspended in 100 ml. ethyl acetate. The suspension is cooled in an ice bath and a stream of anhydrous HCl gas bubbled in for 15 minutes. The HCl gas is purged with nitrogen gas. The solid is filtered, washed with ethyl acetate and dried in vacuo at room temperature to yield 2.10 g. of Phe-Phe-OMe hydrochloride.

Calc. for Phe-PheOMe.HCl: C, 63.06; H, 6.41; N, 7.74. Found: C, 63.00; H, 6.52; N, 7.66.

EXAMPLE 8

Preparation of Asn-Phe-Phe-OMe Hydrochloride

Step a

Phe-Phe-OMe hydrochloride, 12.30 g., is dissolved in 102 ml. freshly degassed DMF. To this solution is added 12.86 g. (7% excess) of BOC-AsnNPE. The pH of the reaction solution is adjusted to 7.2 by the addition of 4.73 ml. of TEA and the solution is stirred overnight.

The reaction solution is concentrated to dryness in vacuo and the residue taken up in chloroform. The chloroform solution is washed with water, saturated sodium bicarbonate solution, 0.1M $H_2SO_4$ and water. The chloroform solution is dried over anhydrous magnesium sulfate and concentrated to dryness. The crude solid residue is dissolved in a minimum amount of hot ethanol. On cooling, the product crystallizes from the ethanol solution. The crystalline product is collected by suction filtration, washed with cold ethanol and dried in vacuo to give 9.18 g. of BOC-Asn-Phe-Phe-OMe.

Step b

BOC-Asn-Phe-Phe-OMe, 8.5 g., is slurried in 110 ml. anhydrous ethyl acetate. This slurry is cooled in an ice bath to 0° C. and a vigorous stream of anhydrous HCl gas is bubbled in for 15 minutes during which time a clear solution is obtained. The solution is purged with a stream of nitrogen gas. Upon the addition of 100 ml. of ether to this solution, the product separates as a solid. The solid is collected by suction filtration, washed with ether (3 × 100 ml.) and dried in vacuo to give 7.27 g. Asn-Phe-Phe-OMe hydrochloride.

EXAMPLE 9

Preparation of (ε-INOC)Lys-Asn-Phe-Phe-OMe Dihydrochloride

Step a

α-BOC-(ε-INOC)Lys, 1.9 g., is dissolved in 50 ml. freshly degassed DMF. To this solution is added 1-hydroxybenzotriazole, 0.675 g. The solution is stirred and cooled in an ice bath. To this cooled solution is added 1.13 g. DCCI. The ice bath is removed and stirring is ontinued for 30 minutes. To this reaction mixture is added Asn-Phe-Phe-OMe hydrochloride, 2.38 g. The pH of the reaction mixture is adjusted to 7.6 by the addition of 1.92 ml. of TEA and the reaction mixture stirred overnight at room temperature.

The reaction mixture is filtered to remove any solids and the filtrate evaporated to dryness in vacuo. The residue is stirred in 800 ml. chloroform, collected by suction filtration and the gelatinous solid washed with chloroform and dried in vacuo to give 1.8 g. α-BOC-(ε-INOC)Lys-Asn-Phe-Phe-OMe. The filtrate and washings are evaporated to dryness in vacuo and the solid residue resuspended in chloroform. The solid is collected by suction filtration, washed with chloroform and dried in vacuo to give an additional 1.82 g. of product.

Step b

α-BOC-(ε-INOC)Lys-Asn-Phe-Phe-OMe, 1 g., is slurried in 13 ml. anhydrous ethyl acetate. The suspension is stirred and cooled in an ice bath. A vigorous stream of anhydrous HCl gas is bubbled into the suspension for 15 minutes after which the suspension is purged with nitrogen gas for 15 minutes. The solid is collected by suction filtration, washed with ethyl acetate and dried in vacuo. The weight of (ε-INOC)Lys-Asn-Phe-Phe-OMe dihydrochloride recovered is 1.04 g.

EXAMPLE 10

Preparation of p-Nitrophenyl Ester of S-Acm-β-mercaptopropionic Acid

S-Acm-β-mercaptopropionic acid, 7.08 g., is dissolved in 100 ml. methylene chloride to which solution is added 5.56 g. p-nitrophenol and 9.48 g. DCCI. The reaction mixture is stirred for 4 hours at room temperature and filtered to remove solids. The solids are washed with methylene chloride and the combined filtrate and washings are washed with sodium bicarbonate solution (2 × 150 ml.). The washed methylene chloride solution is concentrated to a small volume in vacuo. The product crystallizes out and is collected by suction filtration. The product is recrystallized from ethyl acetate:hexane, collected by suction filtration, washed with ethyl acetate:hexane, 25:75, and dried to room temperature in vacuo to yield 3.35 g. of p-nitrophenyl ester of S-Acm-β-mercaptopropionic acid, m.p. 108°–109° C.

Calc. for $C_{12}H_{14}N_2O_5S$: N, 9.39; C, 48.31; H, 4.73; S, 10.75. Found: N, 9.43; C, 48.36; H, 4.79; S, 10.89.

EXAMPLE 11

Preparation of S-Acm-β-mercaptopropionyl-(ε-INOC)Lys-Asn-Phe-Phe-$N_3$

Step a (ε-INOC)Lys-Asn-Phe-Phe-OMe dihydrochloride, 200 mg., is dissolved in 9.0 ml. of freshly degassed DMF. To this solution is added 78 mg. of solid S-Acm-β-mercaptopionylNPE, prepared as described in Example 10. The pH of the resulting solution is adjusted to 8.0 with diisopropylethylamine (DIPEA) and the resulting yellow solution is stirred overnight. The reaction solution is evaporated to dryness in vacuo. The solid residue is stirred in 16 ml. of ethanol for 1 hour and transferred to a centrifuge tube. The suspension is centrifuged and the supernatant decanted. The residue is resuspended in ethanol and centrifuged. The supernatant is decanted. The residue is twice resuspended in 16 ml. ethyl acetate, centrifuged and the supernatant decanted. The residue is dried in vacuo overnight to give 184 mg. of crude product. The crude product is dissolved in a minimum volume of EPAW (10:5:1:3) and applied on a column packed with 20 g. dry Silica Gel H. The column is eluted with EPAW (10:5:1:3) and 20 ml. fractions are collected. The fractions containing the product, as identified by thin layer chromatography, are combined and evaporated to dryness in vacuo. The solid residue is triturated with ethyl acetate, collected by suction filtration and dried in vacuo to yield 134 mg. of the peptide S-Acm-β-mercaptopropionyl-(ε-INOC)Lys-Asn-Phe-Phe-OMe.

Step b

S-Acm-β-mercaptopropionyl-(ε-INOC)Lys-Asn-Phe-Phe-OMe, 130 mg., is dissolved in sufficient methanol: anhydrous hydrazine (2:1) to obtain complete solution. The resulting solution is stirred for 1 hour at room temperature and concentrated to dryness in vacuo. The residue is flushed twice with ethanol. The residue is suspended in ethanol and centrifuged twice. The total volume of ethanol used is 15 ml. The residue is dried in vacuo overnight to yield 107 mg. of S-Acm-β-mercaptopropionyl-(ε-INOC)Lys-Asn-Phe-Phe-$NHNH_2$.

Step c

S-Acm-β-mercaptopropionyl-(ε-INOC)Lys-Asn-Phe-Phe-$NHNH_2$, 107 mg., is slurried in 1 ml. freshly degassed DMF under a nitrogen atmosphere. The slurry is cooled to −25° C. in a methanol-water-Dry Ice bath. To this slurry is added 0.1 ml. of 5.6N HCl in THF. Isoamylnitrite, 13 mg., is added in three portions over a 2-hour period at which time a clear solution is obtained. The S-Acm-β-mercaptopropionyl-(ε-INOC)Lys-Asn-Phe-Phe-$N_3$ in this cold solution is immediately condensed with Trp-(ε-INOC)Lys-Thr-Phe-Thr-Ser-(Acm)Cys-OH dihydrochloride as described below in Example 12

EXAMPLE 12

Preparation of S-Acm-β-mercaptopropionyl-Lys-Asn-Phe-Phe Trp-Lys-Thr-Phe-Thr-Ser-(Acm)Cys-OH Step a To the cold DMF solution of S-Acm-β-mercaptopropionyl-(ε-INOC)Lys-Asn-Phe-Phe-$N_3$, prepared as described in Example 11 above, is added a −25° C. solution of 115 mg. Trp-(ε-INOC)Lys-Thr-Phe-Thr-Ser-(Acm)Cys-OH dihydrochloride in 0.7 ml. DMF. A 0.3 ml. portion of DMF is used as a rinse to facilitate the addition. An additional portion of 0.3 ml. of DMF is added and the pH adjusted to 7.6 with DIPEA. The reaction solution is kept at −5° to 0° C. for 2 days and then concentrated in vacuo to half its volume. Methanol is added to this solution and a solid precipitates. The mixture is centrifuged and the supernatant decanted. The solid is twice resuspended in methanol, centrifuged and the supernatant decanted. The resulting solid is dried in vacuo to obtain 102 mg. of the blocked peptide S-Acm-β-mercaptopropionyl-(ε-INOC)Lys-Asn-Phe-Phe-Trp-(ε-INOC)Lys-Thr-Phe-Thr-Ser-(Acm)Cys-OH.

Step b

Activated zinc dust is prepared by stirring zinc dust, 600 mg., in 1.5 ml. of 2% hydrochloric acid for 1 minute. The zinc dust is collected by filtration and washed with 2% hydrochloric acid (1 × 1.5 ml.), water (3 × 1.5 ml.), ethanol (2 × 1 ml.) and ether (1 × 1 ml.). The activated zinc dust is dried in vacuo at room temperature for ½ hour and ground in a mortar and pestle to remove lumps.

The blocked peptide S-Acm-β-mercaptopropionyl-(ε-INOC)Lys-Asn-Phe-Phe-Trp-(ε-INOC)Lys-Thr-Phe-Thr-Ser-(Acm)Cys-OH, 102 mg., is dissolved in 1.0 ml. 50% aqueous acetic acid with stirring. To this solution is added 100 mg. of freshly-activated Zn dust. The mixture is stirred vigorously for 4 hours. A second portion of activated Zn dust, 100 mg., is added and the mixture stirred overnight at room temperature.

Any unreacted Zn is removed by filtration and washed with 50% aqueous acetic acid. The filtrate and washings containing the product are combined and applied on a 5 cm. × 115 cm. column packed with Sephadex G25 Superfine in 50% aqueous acetic acid. The column is eluted with 50% aqueous acetic acid and 20 ml. portions are collected. Aliquots of the fractions are placed in Quantum Industries Silica Gel H thin layer chromatography plates and developed with EPAW (5:5:1:3). The plates are visualized with t-butylhypochlorite:starch:iodide spray. Those fractions containing material having an $R_f$ value of 0.48 are combined and concentrated to dryness in vacuo. The residue is dissolved in 3 ml. water and lyophilized to give 77 mg. of S-Acm-β-mercaptopropionyl-Lys-Asn-Phe-Phe-Trp-Lys-Thr-Phe-Thr-Ser-(Acm)Cys-OH.

EXAMPLE 13

Preparation of Des(Ala$^1$-Gly$^2$)desaminocys$^3$-somatostatin

Step a

S-Acm-β-mercaptopropionyl-Lys-Asn-Phe-Phe-Trp-Lys-Thr-Phe-Thr-Ser-(Acm)Cys-OH is dissolved in 3.0 ml. of 0.1N acetic acid. To this solution is added a solution containing 29 mg. Hg(OAc)$_2$ in 0.5 ml. 0.1N acetic acid. After stirring the reaction for 1 hour at room temperature under a nitrogen atmosphere, 0.41 ml. of mercaptoethanol is added and stirring continued overnight. The reaction mixture is centrifuged. The supernatant containing the product is decanted. The solid residue is resuspended in 2 ml. 0.1N acetic acid, centrifuged and the supernatant decanted. The combined supernatants are applied on a 2.5 cm. × 100 cm. column packed with Sephadex G-10 in 0.1N acetic acid, developed with 0.1N acetic acid and 20 ml. fractions are collected. The fractions containing the product, as identified by thin layer chromatography, are pooled.

Step b

The pH of this pooled solution is adjusted to 8 with NH$_4$OH, a copper wire loop is placed in the reaction vessel and the reaction stirred vigorously overnight. The copper wire loop is removed, the pH of the blue solution is adjusted to 4.7 with 2 ml. glacial acetic acid and the solution is concentrated to dryness in vacuo. The residue is dissolved in 10 ml. 50% aqueous acetic acid. The light blue colored solution is applied on a 5 cm. × 115 cm. column packed with Sephadex G25 Superfine in 50% aqueous acetic acid, developed with 50% aqueous acetic acid and 10 ml. fractions are collected. The fraction containing the product, as identified by thin layer chromatography, are combined and lyophilized to yield 11.2 mg. of des(Ala$^1$-Gly$^2$)-desaminocys$^3$-somatostatin.

A portion of this product applied on Quantum Industries Silica Gel H thin layer chromatography plates and developed with chloroform:methanol:2% aqueous NaCl solution (50:40:10) shows substantially a single spot at $R_f$0.50 when visualized with t-butylhypochlorite-starch-iodide spray. An aliquot of this material containing 1 μM/0.5 ml. 50% aqueous acetic acid has an ultraviolet absorption maximum at 281 nm and O.D. of 1.885. A quantitative Ellman Assay for free sulfhydryl groups using DNTB showed an O.D. of 0.131 at 412 nm which corresponds to less than 3% free sulfhydryl. A portion of this product, hydrolyzed in acid, indicates the following amino acid analysis:

Lys, 1.95; Asp, 1.05; Thr, 1.99; Ser, 0.866; Phe, 3.18; Trp, 1.0 (determined by U.V.).

EXAMPLE 14

Preparation of Des(Ala$^1$-Gly$^2$)desaminocys$^3$-somatostatin

S-Acm-β-mercaptopropionyl-Lys-Asn-Phe-Phe-Trp-Lys-Thr-Phe-Thr-Ser-(Acm)Cys-OH, 200 mg., is dissolved in 160 ml. of glacial acetic acid containing 120 drops of water. To this solution is added a solution containing 78 mg. of I$_2$ in 40 ml. of glacial acetic acid. The resulting solution is stirred magnetically at room temperature for 7 days. Sodium thiosulfate, Na$_2$S$_2$O$_3$, is added to discharge the excess iodine. The solution is concentrated to dryness in vacuo. The residue is dissolved in 5 ml. of 50% aqueous acetic acid and applied on a 5 cm. × 115 cm. column packed with Sephadex G25 Superfine in 50% aqueous acetic acid. The column is eluted with 50% aqueous acetic acid and 20 ml. fractions are collected. The fractions containing the product, as determined by thin layer chromatography, are combined and lyophilized to give 112 mg. of des(Ala$^1$-Gly$^2$)desaminocys$^3$-somatostatin.

Des(Ala$^1$-Gly$^2$)desaminocys$^3$-somatostatin is useful in humans and animals for inhibiting gastric secretion in the treatment of gastric ulcers, inhibiting growth hormone release as in the treatment of acromegaly and alone or in conjunction with insulin, for lowering blood glucose as in the treatment of diabetes. In the treatment of diabetes, the number and size of daily doses and the time of administration are determined by an individual study of each subject. The method of determining these factors is known to those skilled in the art.

The somatostatin analog described herein may be administered to warm blooded animals, including humans, either intravenously, subcutaneously, intramuscularly or orally. The contemplated dose range for oral administration in tablet or capsule form to large mammals is about 0.001 mg. to about 7 mg./kg. of body weight per day. This somatostatin analog is preferably administered by injection. A therapeutically effective amount of the analog is ordinarily supplied at a dosage level of from about 0.001 mg. to about 2 mg/kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following Example is included to illustrate the preparation of a representative dose of des(Ala$^1$-Gly$^2$)-desaminocys$^3$-somatostatin suitable for subcutaneous injection.

EXAMPLE 15

1ml. sterile saline;
1 mg. des(Ala$^1$-Gly$^2$)desaminocys$^3$-somatostatin.

What is claimed is:

1. The peptide having the structure: S-Acm-β-mercaptopropionyl-(ε-INOC)Lys-Asn-Phe-Phe-Trp-(ε-INOC)Lys-Thr-Phe-Thr-Ser-(Acm)Cys-OH.

2. The peptide having the structure: S-Acm-β-mercaptopropionyl-Lys-Asn-Phe-Phe-Trp-Lys-Thr-Phe-Thr-Ser-(Acm)Cys-OH.

3. The process of preparing the peptide having the structure β-mercaptopropionyl-Lys-Asn-Phe-Phe-Trp-Lys-Thr-Phe-Thr-Ser-Cys-OH which comprises treating the peptide having the amino acid sequence S-Acm-β-mercaptopropionyl-Lys-Asn-Phe-Phe-Trp-Lys-Thr-Phe-Thr-Ser-(Acm)Cys-OH with iodine.

4. The process of preparing the peptide having the structure β-mercaptopropionyl-Lys-Asn-Phe-Phe-Trp-Lys-Thr-Phe-Thr-Ser-Cys-OH which comprises treating the peptide having the amino acid sequence β-mercaptopropionyl-Lys-Asn-Phe-Phe-Trp-Lys-Thr-Phe-Thr-Ser-Cys-OH by stirring a solution containing said peptide in the presence of atmospheric oxygen and copper ion.

5. The process of preparing the peptide of claim 1 wherein the process comprises forming the active ester of the peptide having the amino acid sequence S-Acm-β-mercaptopropionyl-(ε-INOC)Lys-Asn-Phe-Phe-OH and reacting said active ester with the amino group of the tryptophan residue of the peptide having the amino acid sequence Trp-(ε-INOC)Lys-Thr-Phe-Thr-Ser-(Acm)Cys.

6. The process of preparing the peptide of claim 1 wherein the process comprises forming the azide of the peptide having the amino acid sequence S-Acm-β-mercaptopropionyl-(ε-INOC)Lys-Asn-Phe-Phe-OMe and reacting said azide with the amino group of the tryptophan residue of the peptide having the amino acid sequence Trp-(ε-INOC)Lys-Thr-Phe-Thr-Ser-(Acm)Cys.

7. The process of preparing the peptide having the structure: S-Acm-β-mercaptopropionyl-(ε-INOC)Lys-Asn-Phe-Phe-OMe wherein the process comprises treating the peptide (ε-INOC)Lys-Asn-Phe-Phe-OMe with S-Acm-β-mercaptopropionyl NPE.

8. The process of preparing the peptide of claim 2 wherein the process comprises treating the peptide having the amino acid sequence Acm-β-mercaptopropionyl-(ε-INOC)Lys-Asn-Phe-Phe-Trp-(ε-INOC)Lys-Thr-Phe-Thr-Ser-(Acm)Cys-OH with zinc dust.

9. The process for preparing the peptide having the structure: β-mercaptopropionyl-Lys-Asn-Phe-Phe-Trp-Lys-Thr-Phe-Thr-Ser-Cys-OH wherein the process comprises treating the peptide having the amino acid structure: S-Acm-β-mercaptopropionyl-Lys-Asn-Phe-Phe-Trp-Lys-Thr-Phe-Thr-Ser-(Acm)Cys-OH with mercuric ion.

* * * * *